(12) United States Patent
Chen

(10) Patent No.: US 11,684,259 B2
(45) Date of Patent: Jun. 27, 2023

(54) PUPILLOMETER FOR LESION LOCATION DETERMINATION

(71) Applicant: Purdue Research Foundation, West Lafayette, IN (US)

(72) Inventor: Bin Chen, Munster, IN (US)

(73) Assignee: Purdue Research Foundation, West Lafayette, IN (US)

( * ) Notice: Subject to any disclaimer, the term of this patent is extended or adjusted under 35 U.S.C. 154(b) by 734 days.

(21) Appl. No.: 16/676,859

(22) Filed: Nov. 7, 2019

(65) Prior Publication Data

US 2020/0205660 A1   Jul. 2, 2020

Related U.S. Application Data

(60) Provisional application No. 62/787,416, filed on Jan. 2, 2019.

(51) Int. Cl.
| | |
|---|---|
| *A61B 3/18* | (2006.01) |
| *A61B 3/15* | (2006.01) |
| *A61B 3/14* | (2006.01) |
| *A61B 5/00* | (2006.01) |
| *A61B 3/00* | (2006.01) |
| *A61B 3/11* | (2006.01) |

(52) U.S. Cl.
CPC .............. *A61B 3/18* (2013.01); *A61B 3/0008* (2013.01); *A61B 3/112* (2013.01); *A61B 3/145* (2013.01); *A61B 3/156* (2013.01); *A61B 5/4064* (2013.01); *A61B 2576/026* (2013.01)

(58) Field of Classification Search
CPC ......... A61B 3/18; A61B 3/0008; A61B 3/112; A61B 3/145; A61B 3/156; A61B 5/4064; A61B 2576/026
USPC ........................................................ 600/473
See application file for complete search history.

(56) References Cited

U.S. PATENT DOCUMENTS

| | | | | |
|---|---|---|---|---|
| 8,911,085 | B2* | 12/2014 | Privitera | A61B 5/7203 351/200 |
| 9,872,616 | B2* | 1/2018 | Daneshi Kohan | A61B 3/0033 |
| 11,071,596 | B2* | 7/2021 | Ryan | A61B 34/25 |
| 2004/0090524 | A1* | 5/2004 | Belliveau | H05B 47/18 348/E5.143 |
| 2010/0220286 | A1* | 9/2010 | Nauche | A61B 3/111 351/204 |

OTHER PUBLICATIONS

Traustason, S., Pupillary response to direct and consensual chromatic light stimuli. Acta Ophthalmologica 2016, 65-69.

* cited by examiner

*Primary Examiner* — Mohammed A Hasan
(74) *Attorney, Agent, or Firm* — Purdue Research Foundation

(57) ABSTRACT

The present disclosure relates to a novel pupilometer and method of using the pupilometer to record and analyze direct and consensual reflex of pupils to identify brain lesion locations of a patient with brain injuries.

4 Claims, 7 Drawing Sheets

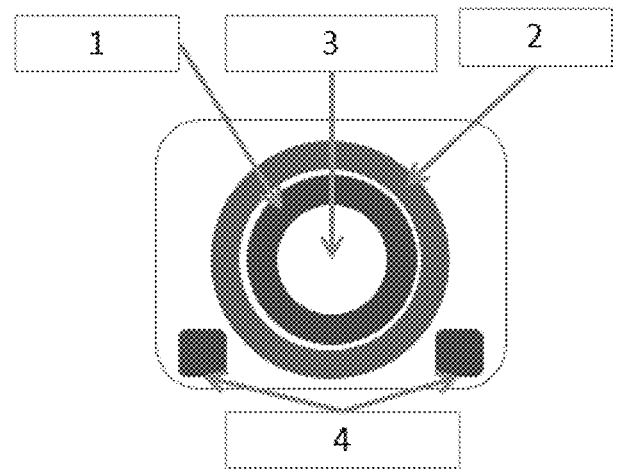
FIG. 3A
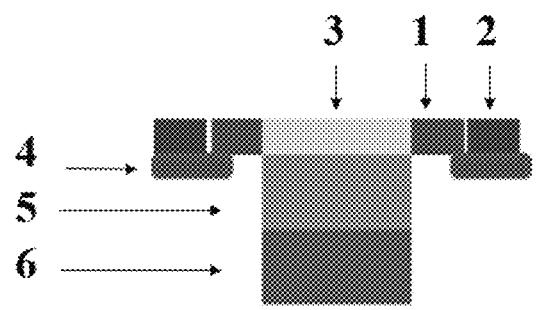
FIG. 3B
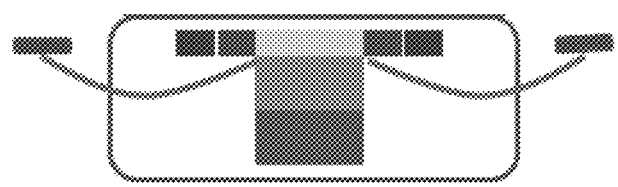
FIG. 3C
FIG. 3

PUPILLOMETER FOR LESION LOCATION DETERMINATION

CROSS-REFERENCE TO RELATED APPLICATION

This application claims the benefits of U.S. Provisional Application Ser. No. 62/787,416 filed Jan. 2, 2019, the contents of which are incorporated herein entirely.

TECHNICAL FIELD

The present disclosure relates to a novel pupilometer and method of using the pupilometer to record and analyze direct and consensual reflex of pupils to identify brain lesion locations of a patient with brain injuries.

BACKGROUND

This section introduces aspects that may help facilitate a better understanding of the disclosure. Accordingly, these statements are to be read in this light and are not to be understood as admissions about what is or is not prior art.

Checking pupil size and reactivity to light (pupillary light reflex) is a routine for doctors in the neurological examination and monitoring of patients with brain injury or stroke. It is widely used as a vital indicator for quick brain injury assessment or prompt medical intervention. Patients have a better chance of rescue or recovery when abnormal pupillary reflex patterns are detected.

An electronic pupillometer minimizes doctors' variability and subjectivity from the evaluation with a flashlight by providing accurate numerical pupil sizes and reflex trends allowing earlier detection of abnormal pupillary reflex changes for more timely patient treatment. The digital pupillometers can be classified into two groups: binocular-shaped pupillometer and flashlight-shaped pupillometer. Binocular-shaped pupillometers are usually used by ophthalmologists or optometrists (FIG. 1). The pupillometers most widely used in clinical environments are single lens flashlight-like pupillometer which has an advanced optical imaging system and algorithms to determine the pupillary light responses (FIG. 2). (The pupillometer in this disclosure refers the electronic flashlight-like pupillometer.)

Current pupillometers on the market exam left and right eyes independently. Therefore, only direct pupillary light response of each eye is measured. While the measurement of direct pupillary light reflex can determine the pupil size and the constrict process when the eye is illuminated, it cannot get the consensual light response which needs to shine light on the other eye. Because both direct and consensual pupillary light responses are required for most disease diagnosis and lesion location determination, pupillometers currently on the market cannot diagnose majority of diseases or estimate lesion locations.

Therefore, there is an unmet need for pupillometers that can efficiently and accurately measure both direct and consensual light responses with a single device.

SUMMARY

The present disclosure relates to a novel pupilometer and method of using the pupilometer to record and analyze direct and consensual reflex of pupils to identify brain lesion locations of a patient with brain injuries.

In one embodiment, the present disclosure provides a novel pupilometer device, wherein the device comprises:

a housing;
an imaging device in the housing;
a set of infrared light sources in the housing for image and/or video acquisition;
an infrared light filter in the housing that allows the pass of infrared light and substantially blocks all visible lights;
a first visible light source in the housing that is capable of providing a visible light to the first eye of a patient;
a second visible light source that is outside of the housing and is capable of providing a visible light to the second eye of the patient when the imaging device is simultaneously taking image and/or video from the first eye, wherein the second visible light source is extendable from the housing and is capable of reaching the second eye; and
a control system configured to manipulate the visible light source, the infrared light source and the imaging device;
wherein the infrared light source in the housing is capable of continuously illuminating the first and/or second eye of the patient with infrared light from the infrared light source during a test to provide the necessary illumination for image/video acquisition.

In one embodiment, the present disclosure provides a novel method to use the pupilometer device of the present disclosure to efficiently and accurately measure both direct and consensual light responses with a single device, and analyze the acquired data to determine whether there is lesion in the brain and the location of the injured nerves.

BRIEF DESCRIPTION OF THE DRAWINGS

FIG. 3 shows schematic diagram of the main components of the device of the present disclosure. FIG. 3A is the front view of the device. FIG. 3B is the top sectional view of the device when the extendable light is at the original non-extended position. FIG. 3C is the top sectional view of the device when the extendable light is at the extended position. Visible lights are to illuminate a pupil. The expandable arm is to extend the visible light to illuminate the contralateral eye. Visible light ring is to illuminate the ipsilateral eye. IR light ring is for image and video acquisition illumination.

DETAILED DESCRIPTION

Figure 1:
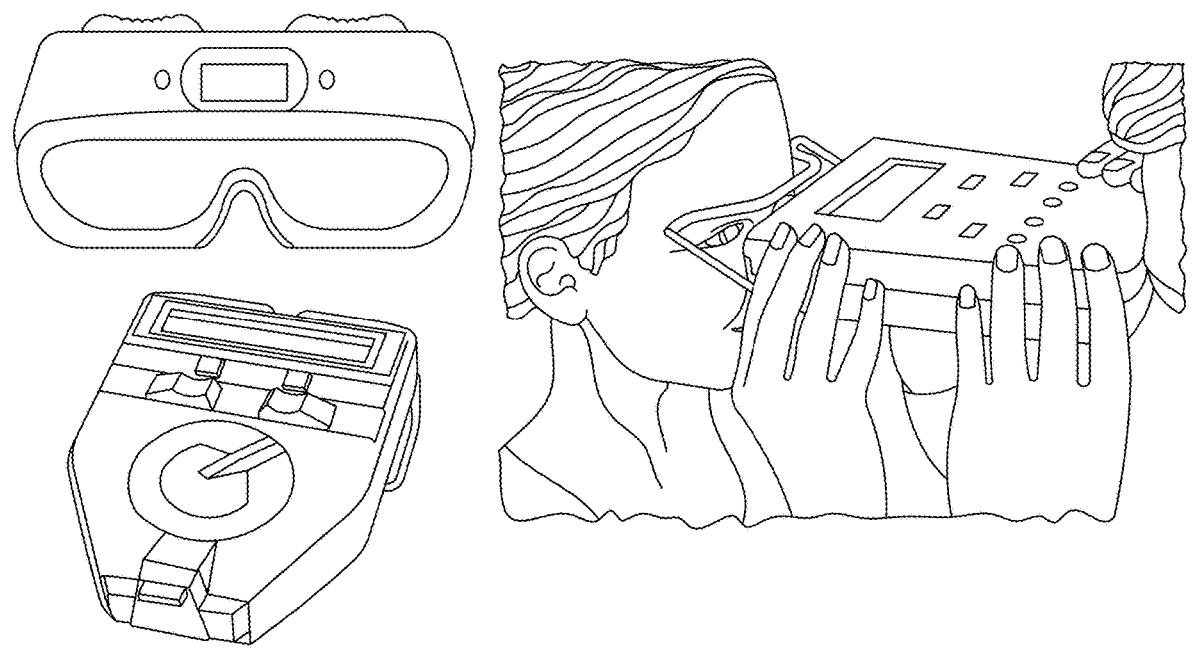
FIG. 1 shows a binocular shaped pupilometer that is commonly used by ophthalmologists.
Figure 2:
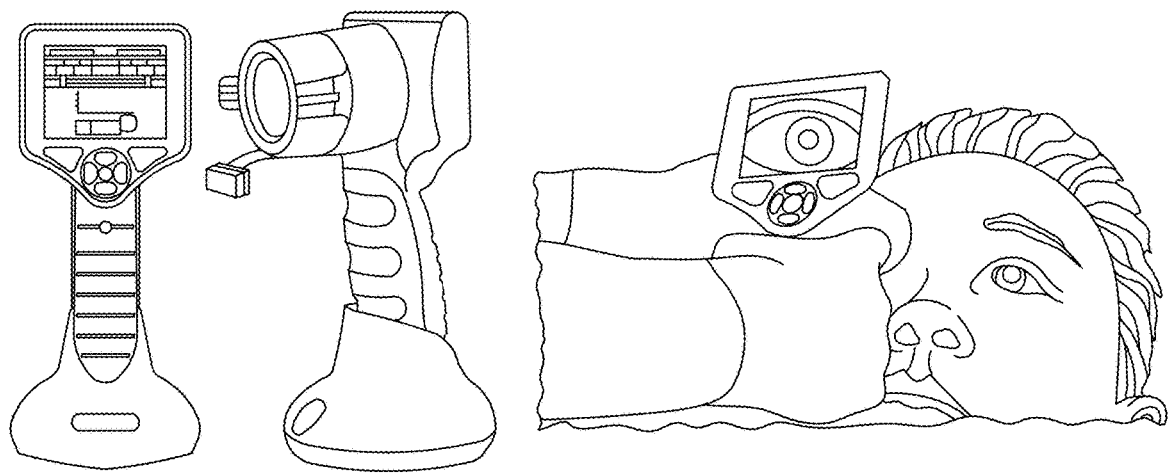
FIG. 2 shows a flashlight like pupilometer that is commonly in urgent care and/or emergency rooms.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The present disclosure provides novel functions not existing in the pupillometers currently on the market such as NeurOptics' NPi®-200 Pupillometer.

The present disclosure provides a novel device that has the capability of determining all possible lesion sites from pupillary reflex. Current pupillometers on the market exam left and right eyes independently. Therefore, only direct pupillary light response of each eye is measured. While the measurement of direct pupillary light reflex may determine the pupil size and the constrict process when the eye is illuminated, it cannot get the consensual light response which needs to shine light on the other eye. Because both direct and consensual pupillary light responses are required for most disease diagnosis and lesion location determination. Pupillometers currently on the market cannot diagnose majority of disease or estimate lesion locations This present disclosure provides novel device and method that can measure both direct and consensual light responses for disease diagnosis and classification, and lesion location estimation. It will be ideal for evaluating optical nerve and oculomotor nerve integrity, brain stem assessment and lesion localization estimation for clinical applications in emergency rooms, critical care, and ambulances.

The following Table 1 shows the new functions of the invention in comparison with NeurOptics' Pupillometer.

TABLE 1

| NeurOptics Pupillometer | This present disclosure |
| --- | --- |
| Measure each eye independently. Unable to detect the symptoms when referencing consensual pupillary reflex is needed. | Acquire both direct and consensual pupillary reflexes with controlled light stimulus schemes. Able to detect all abnormal pupillary reflex changes. |
| Estimate the pupil size and shape with traditional contour detection algorithms. Does not provide the information of lesion sites. | Use deep learning to track the pupil reflex. Provide lesion sites. |

Methods

Schematic Diagram

As illustrated in FIG. 3a-3c, a set of visible lights (one or more) 1 and a set of infrared lights (one or more) 2 located on the main body (housing) are provided for pupil illumination and IR image acquisition respectively. An IR filter 3 in front of the lens is an infrared pass filter which removes all visible lights. The visible lights 1 in the main body (housing) are to illuminate a pupil. The expandable visible light system 4 can illuminate a contralateral eye. There can be at least one expandable visible light. For convenience purpose, two expandable visible lights can be provided as shown in FIG. 3A. Other designs for the same purpose may be achieved. For example, a rotatable arm with a center/base on the main body (housing) of the device may just need one rotatable arm to provide the visible light to either left or right side eyes when the corresponding consensual response of right or left eye is recorded. The set of IR lights 2 are provided for image and/or video acquisition.

Figure 5:
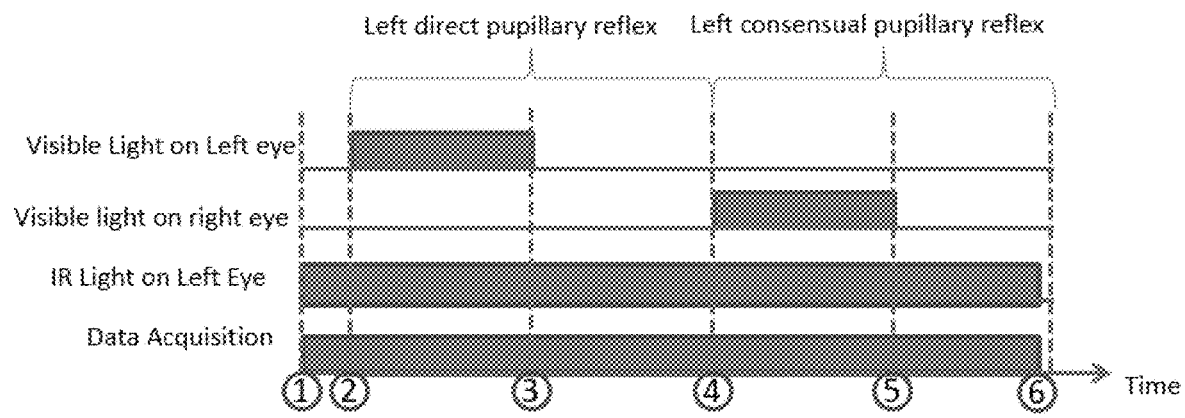
FIG. 5 shows left eye pupillary reflex measurement. The number in a circle represents the light on or off time point during an exam.

In the top sectional views of the device as shown in FIGS. 3B and 3C, 5 is an image and/or video acquisition component, and 6 is a data processing component. FIG. 3B is the top sectional view of the device when the extendable light is at the original non-extended position. FIG. 3C is the top sectional view of the device when the extendable light is at the extended position. In FIG. 3C, the left side extendable light is configured to extend to illuminate the left eye for right consensual reflex acquisition, and the right side extendable light is configured to extend to illuminate the right eye for left consensual reflex acquisition. In FIG. 3A-3C, the illustrated visible light and IR light systems are ring shaped system. However, it should be understood that other kind of shapes for visible light and IR light systems may be used.

Figure 4:
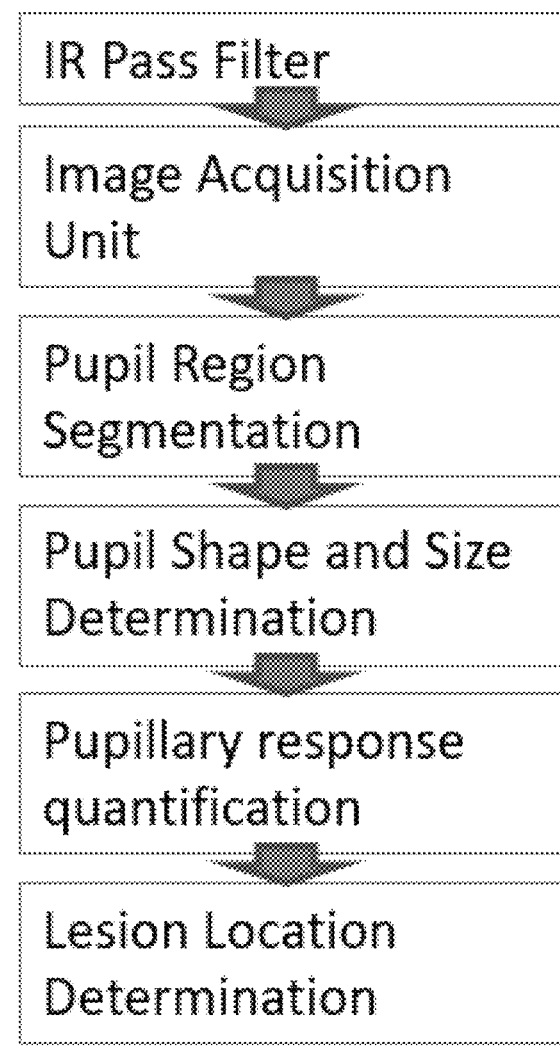
FIG. 4 shows the flow of pupillary response measurement and lesion location determination.

The processing flow scheme is shown in FIG. 4.

The image and video acquisition system is to record pupil size constriction and dilation during pupillary reflex. It consists of the light subsystem and image/video acquisition subsystem.

The light subsystem uses two types of lights: 1) visible light as stimulus for pupillary reflex activation and stimulation (Visible light); 2) Infrared light for image and video acquisition (IR light). Using IR light for data acquisition has the following advantages:
 a) The device can work on any light conditions even in very dim or dark environments;
 b) The invisible IR lights will not interfere with the stimulus lights or affect pupillary reflex because it only responses to visible lights; and
 c) The acquired IR images/videos will have the consistent contrast and patterns after removing the visible light during the image acquisition.

Figure 6:
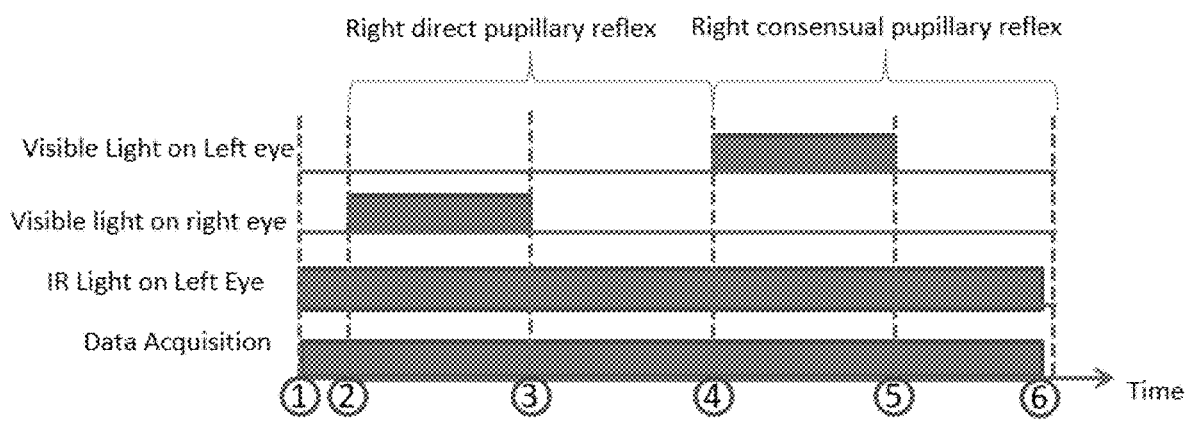
FIG. 6 shows right eye pupillary reflex measurement. The number in a circle represents the light on or off time point during an exam.

The image/video acquisition procedures are shown in FIG. 5 and FIG. 6 for the measurements of left and right eyes, respectively. The timing points below are indicated in circular markers.

Circle 1: Aim the device to one eye (the left eye for example) and start the exam. IR light is on and the data acquisition is on during the whole process.

Circle 2: The visible light shining on the left eye is on. The pupil starts to constrict for healthy subjects due to the pupillary reflex response.

Circle 3: The visible light is off. The pupil starts to dilate.

Circle 4: The visible light shining on the right eye is on (the opposite eye). The device keeps recording the pupillary response of the left eye to the illumination on the right eye. (consensual response).

Circle 5: The visible light is off. The pupil starts to dilate.

Circle 6: IR light is off. Data acquisition stops.

Pupil Size and Shape Determination

Tremendous progresses have been made in image analysis primarily due to recent breakthroughs of deep learning. Deep learning allows multiple levels of feature abstraction using models composed of multiple learning layers. It has dramatically pushed the limits of the-state-of-the-art levels in image processing and computer vision, the first and most successful application area of deep learning.

The pupil shape and size are determined by a fast convolutional neural network. The network was trained by a large number of manually segmented left and right eye images. This deep learning based technique has achieved 100% accuracy in finding the shape and size of pupils.

Lesion Location Estimation

There are four types of pupillary light reflex responses: 1) Left direct pupillary reflex: The left pupil's response when the left eye is illuminated; 2) Left consensual pupillary reflex: The left pupil's response when the right eye is illuminated; 3) Right direct pupillary reflex: The right pupil's response when the right eye is illuminated; and 4) Right consensual pupillary reflex: The right pupil's response when the left eye is illuminated.

Figure 7:
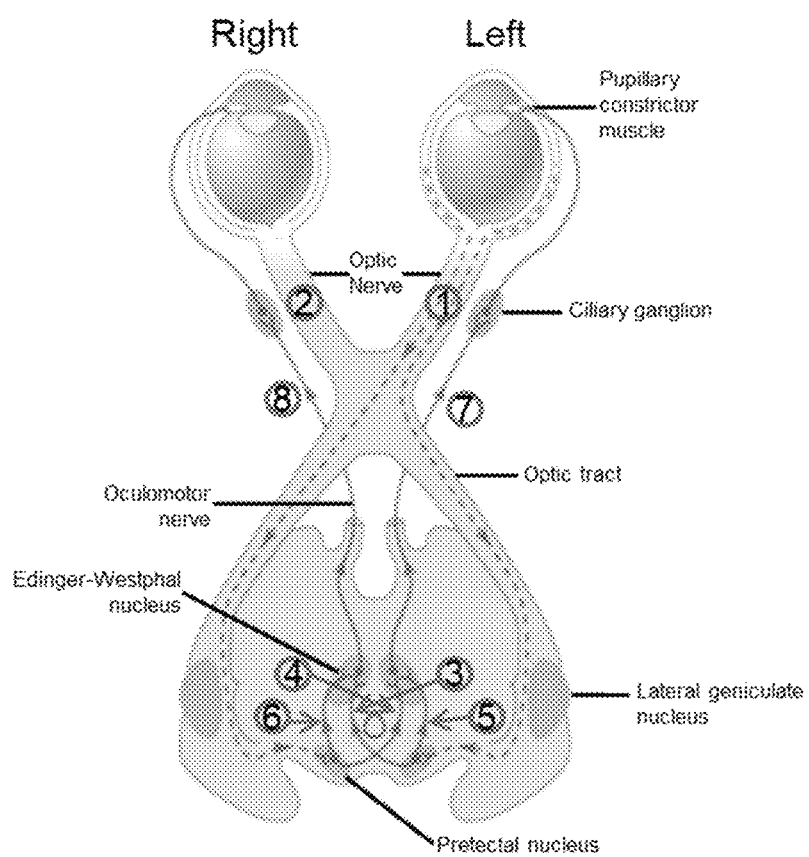
FIG. 7 shows the pupillary light reflex neural pathway and neural segments.

The neural pathway is consisted by four main neural segments for each side, which can be numbered from 1 to 8 with odd numbered segments for the left side and even numbered segments for the right side by convention. In FIG. 7, Number 1, 2 are optic nerve (CN II), Number 7, 8 are oculomotor nerve (CN III) and Number 3, 4, 5, 6 represents internuncial neural fibers between Pretctal Nucles and Edinger Westphal Nucleus in Mid Brain. FIG. 7 shows the eight neural segments of the pathway.

Each pupillary reflex response is either normal or abnormal. Therefore, there are a total of 16 cases for possible direct and consensual pupillary reflex responses of both eyes. Only 10 unique cases when the symmetrical pathway between the left and right side is considered. The rest 6 cases are mirrors between left and right eyes. When the pupillary responses for both eyes are acquired, the possible lesion locations can be determined or estimated. Table 2 provides all 16 cases for pupillary responses.

TABLE 2

All 16 cases for pupillary responses and lesion location estimation

| Case | Left Direct | Left Consensual | Right Direct | Right Consensual | Lesion Locations* |
|---|---|---|---|---|---|
| 1 | Normal | Normal | Normal | Normal | Normal |
| 2 | Normal | Abnormal | Normal | Normal | 4 |
| 3 | Abnormal | Normal | Normal | Normal | 5 |
| 4 | Normal | Normal | Abnormal | Normal | 6 |
| 5 | Normal | Normal | Abnormal | Abnormal | 8 |
| 6 | Normal | Normal | Normal | Abnormal | 3 |
| 7 | Normal | Abnormal | Abnormal | Normal | 2 |
| 8 | Abnormal | Normal | Normal | Abnormal | 1 |
| 9 | Abnormal | Abnormal | Normal | Normal | 7 |
| 10 | Normal | Abnormal | Normal | Abnormal | (3, 4) |
| 11 | Abnormal | Normal | Abnormal | Normal | (5, 6) |
| 12 | Abnormal | Normal | Abnormal | Abnormal | (1, 8), (1, 6), (5, 8) |
| 13 | Normal | Abnormal | Abnormal | Abnormal | (2, 8), (2, 3), (4, 8) |
| 14 | Abnormal | Abnormal | Normal | Abnormal | (1, 7), (1, 4), (3, 7) |
| 15 | Abnormal | Abnormal | Abnormal | Normal | (2, 7), (2, 5), (6, 7) |
| 16 | Abnormal | Abnormal | Abnormal | Abnormal | (1, 2), (7, 8) etc . . . |

*Note:
For example (1, 7) stands for the lesion locations in the neural segment 1 and 7

Figure 8:
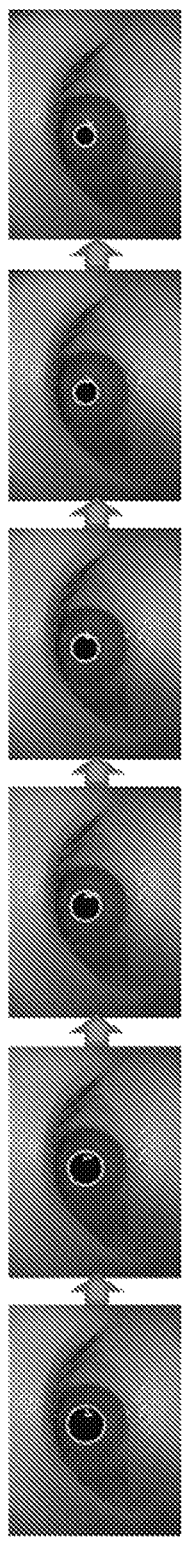
FIG. 8 shows an actual measurement of pupillary light reflex, which can be determined in approximately 1 second. While pupil constrict may require 4 seconds to reach the plateau).

FIG. 8 shows an actual measurement of pupillary light reflex, which can be determined in approximately 1 second.

Figure 9:
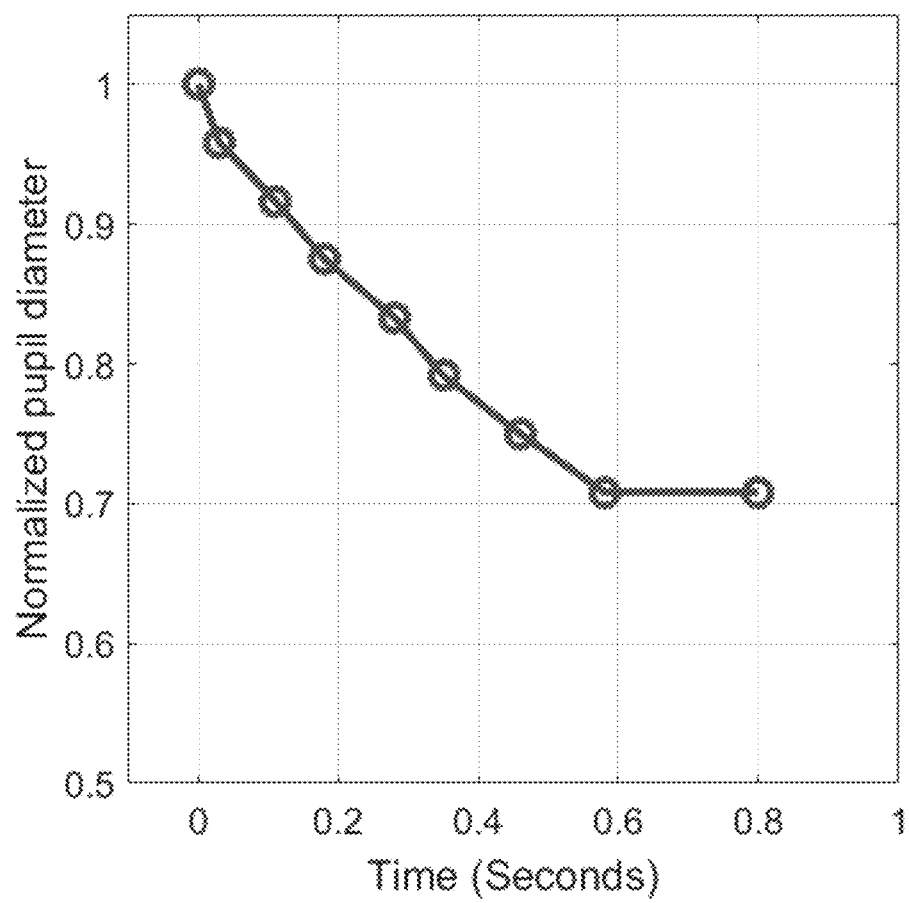
FIG. 9 shows the data for the pupil's response to lights against the time.

FIG. 9 shows the data for the pupil's response to lights against the time.

In one embodiment, the present disclosure provides a novel pupilometer device, wherein the device comprises:
a housing;
an imaging device in the housing;
a set of infrared light sources in the housing for image and/or video acquisition;
an infrared light filter in the housing that allows the pass of infrared light and substantially blocks all visible lights;
a first visible light source in the housing that is capable of providing a visible light to the first eye of a patient;
a second visible light source that is outside of the housing and is capable of providing a visible light to the second eye of the patient when the imaging device is simultaneously taking image and/or video from the first eye, wherein the second visible light source is extendable from the housing and is capable of reaching the second eye; and
a control system configured to manipulate the visible light source, the infrared light source and the imaging device;
wherein the infrared light source in the housing is capable of continuously illuminating the first and/or second eye of the patient with infrared light from the infrared light source during a test to provide the necessary illumination for the illumination.

In one embodiment, the present disclosure provides a novel pupilometer device, wherein the device comprises an optional third visible light source that is outside of the housing, is extendable from the housing, and is capable of reaching to the second eye, wherein the second and the third visible light sources are designed to ensure the second and the third visible light sources capable of provide visible light to either eye when the image/video of other eye is being captured.

In one embodiment, the present disclosure provides a method of detecting lesion location of brain nerves through pupillary reflex, wherein the method comprises:
aiming the device of the present disclosure to a first eye of a patient;
continuously illuminating the first eye of the patient with the infrared light from the infrared light source for imaging device to capture image/video or image/video related data of the pupillary reflex from the first eye;
turning on the first visible light to the first eye and capturing image/video or image/video related data of the direct pupillary reflex response of the first eye trigged by the visible light from the first visible light source;
turning off the first visible light and allowing the pupil of the first eye to dilate;
keeping aiming the device of the present disclosure to the first eye of the patient, and
aiming the second or third visible light to the second eye of the patient, turning on the second or third visible light and recording the consensual pupillary reflex response of the first eye trigged by the second or third visible light applied on the second eye;
aiming the device of the present disclosure to the second eye of a patient;
continuously illuminating the second eye of the patient with the infrared light from the infrared light source for imaging device to capture image/video or image/video related data of the pupillary reflex from the second eye;
turning on the first visible light to the second eye and recording the direct pupillary reflex response of the second eye trigged by the visible light from the first visible light source;
turning off the first visible light and allowing the pupil of the second eye to dilate;
keeping aiming the device of the present disclosure to the second eye of the patient, and
aiming the second or third visible light to the first eye of the patient, turning on the second or third visible light and recording the consensual pupillary reflex response of the second eye trigged by the second or third visible light.

In one embodiment, the present disclosure provides a method of detecting lesion location of brain nerves through pupillary reflex, wherein the method further comprises analysis of the acquired image/video or image/video related data and determine lesion location of brain nerves.

Those skilled in the art will recognize that numerous modifications can be made to the specific implementations described above. The implementations should not be limited to the particular limitations described. Other implementations may be possible.

I claim:

1. An electronic flashlight-like pupillometer for measurement of direct and consensual pupillary light responses of the eyes of a patient, which pupillometer comprises:
   a housing;
   an imaging device in the housing;
   a set of infrared light sources in the housing for image and/or video acquisition;
   an infrared light filter in front of the imaging device in the housing that allows the passage of infrared light and substantially blocks all visible lights;
   a first visible light source in the housing that can provide a visible light to the first eye of the patient;
   a second visible light source that is outside of the housing, extendable from the housing, and can provide a visible light to the second eye of the patient when the imaging device is simultaneously taking image and/or video of the first eye;
   an image and/or video acquisition component consisting of a light subsystem and an image/video acquisition subsystem configured to manipulate the visible light source, the infrared light source, and the imaging device for acquiring image/video from both eyes, and recording direct and consensual pupillary reflex response:
   and
   a data processing component configured to determine pupil size and shape using a convolution neural network and to quantify pupillary response for disease diagnosis and determination of lesion locations;
   wherein the infrared light source in the housing can continuously illuminate the first and/or second eye of the patient with infrared light from the infrared light source during a test to provide the necessary illumination for the image/video acquisition.

2. The device of claim 1, wherein the device comprises an optional third visible light source that is outside of the housing, is extendable from the housing, and can provide visible light to the second eye, and the second and the third visible light sources are designed to ensure the second and the third visible light sources can provide visible light to either eye when the image/video of the other eye is being captured.

3. A method of detecting lesion location of brain nerves through pupillary reflex, wherein the method comprises;
   aiming the device of claim 1 to a first eye of a patient to measure a pupillary reflex;
   continuously illuminating the first eye of the patient with the infrared light from the infrared light source for imaging device to capture image/video or image/video related data of the pupillary reflex from the first eye;
   turning on the first visible light to the first eye and capturing image/video or image/video related data of the direct pupillary reflex response of the first eye triggered by the visible light from the first visible light source;
   turning off the first visible light and allowing the pupil of the first eye to dilate;
   keep aiming the device of claim 1 to the first eye of the patient to measure a pupillary reflex, and aiming the second or third visible light to the second eye of the patient, turning on the second or third visible light and recording the consensual pupillary reflex response of the first eye triggered by the second or third visible light applied on the second eye;
   aiming the device of claim 1 to the second eye of a patient to measure a pupillary reflex,
   continuously illuminating the second eye of the patient with the infrared light from the infrared light source for imaging device to capture image/video or image/video related data of the pupillary reflex from the second eye;
   turning on the first visible light to the second eye and recording the direct pupillary reflex response of the second eye triggered by the visible light from the first visible light source;
   turning off the first visible light and allowing the pupil of the second eye to dilate;
   keep aiming the device of claim 1 to the second eye of the patient to measure a pupillary reflex and aiming the second or third visible light to the first eye of the patient, turning on the second or third visible light and recording the consensual pupillary reflex response of the second eye triggered by the second or third visible light.

4. The method of claim 3, wherein the method further comprises analyzing the acquired image/video or image/video related data and determining lesion location of brain nerves.

* * * * *